(12) United States Patent
Lewandowski et al.

(10) Patent No.: US 8,552,130 B2
(45) Date of Patent: *Oct. 8, 2013

(54) POLYMERIZABLE IONIC LIQUID COMPRISING AROMATIC CARBOXYLATE ANION

(75) Inventors: Kevin M. Lewandowski, Inver Grove Heights, MN (US); Yizhong Wang, Woodbury, MN (US); Larry R. Krepski, White Bear Lake, MN (US); Joel D. Oxman, Minneapolis, MN (US); Peiwang Zhu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/579,153

(22) PCT Filed: May 16, 2011

(86) PCT No.: PCT/US2011/036586
§ 371 (c)(1),
(2), (4) Date: Aug. 15, 2012

(87) PCT Pub. No.: WO2011/146356
PCT Pub. Date: Nov. 24, 2011

(65) Prior Publication Data
US 2013/0059975 A1 Mar. 7, 2013

Related U.S. Application Data

(60) Provisional application No. 61/360,139, filed on Jun. 30, 2010, provisional application No. 61/345,624, filed on May 18, 2010.

(51) Int. Cl.
*C08F 26/00* (2006.01)
*C08F 12/30* (2006.01)
*C08F 118/02* (2006.01)
*A61K 6/00* (2006.01)

(52) U.S. Cl.
USPC ........... 526/263; 526/287; 526/312; 526/319; 523/118; 522/167; 522/173

(58) Field of Classification Search
USPC .............. 526/263, 287, 312, 319; 523/118; 522/167, 173
See application file for complete search history.

(56) References Cited

U.S. PATENT DOCUMENTS

| | | |
|---|---|---|
| 3,780,092 A | 12/1973 | Samour |
| 4,262,072 A | 4/1981 | Wendling |
| 4,503,169 A | 3/1985 | Randklev |
| 4,933,405 A | 6/1990 | Evani |
| 5,130,347 A | 7/1992 | Mitra |
| 5,154,762 A | 10/1992 | Mitra |
| 5,159,035 A | 10/1992 | Evani |
| 5,501,727 A | 3/1996 | Wang |
| 5,534,322 A | 7/1996 | Ueyama |
| 5,545,676 A | 8/1996 | Palazzotto |
| 6,030,606 A | 2/2000 | Holmes |
| 6,428,862 B1 | 8/2002 | Noguchi |
| 6,730,156 B1 | 5/2004 | Windisch |
| 7,090,721 B2 | 8/2006 | Craig |
| 7,090,722 B2 | 8/2006 | Budd |
| 7,156,911 B2 | 1/2007 | Kangas |
| 7,553,881 B2 | 6/2009 | Salz |
| 7,649,029 B2 | 1/2010 | Kolb |
| 2007/0194275 A1 | 8/2007 | Masuda |
| 2008/0051605 A1 | 2/2008 | Ricks-Laskoski |
| 2008/0125559 A1 | 5/2008 | Radosz |
| 2008/0134895 A1 | 6/2008 | Ruud |
| 2008/0182917 A1 | 7/2008 | Miyabayashi |
| 2008/0224089 A1 | 9/2008 | Pei |
| 2009/0030158 A1* | 1/2009 | Amano et al. ............ 525/403 |
| 2010/0051509 A1* | 3/2010 | Martinez et al. ........ 208/237 |

FOREIGN PATENT DOCUMENTS

| | | |
|---|---|---|
| EP | 1116769 | 7/2001 |
| GB | 2449926 | 12/2008 |
| JP | 5-98049 | 4/1993 |
| JP | 5-163317 | 6/1993 |
| JP | 6-128501 | 5/1994 |
| JP | 6-180859 | 6/1994 |
| JP | 9-268260 | 10/1997 |
| JP | 2004-255481 | 9/2004 |
| JP | 2005-223967 | 8/2005 |
| JP | 2005-255843 | 9/2005 |
| JP | 2006/137885 | 6/2006 |
| JP | 2007/308616 | 11/2007 |
| JP | 2009/049397 | 3/2009 |
| WO | WO 2006/026064 | 3/2006 |
| WO | WO 2006/053083 | 5/2006 |

(Continued)

OTHER PUBLICATIONS

Abedin et al., "Ionic Liquids: The Link to High-Temperature Molten Salts?", Accounts of Chemical Research, 2007, 40, 1106-1113.
Anderson et al., "Solubility of $CO_2$, $CH_4$, $C_2H_6$, $C_2H_4$, $O_2$, and $N_2$ in 1-Hexyl-3methylpyridinium Bis(trifluoromethylsulfonyl)imide: Comparison to Other Ionic Liquids", Accounts of Chemical Research, 2007, 40, 1208-1216.
Angell et al., "Parallel Developments in Aprotic and Protic Ionic Liquids: Physical Chemistry and Applications", Accounts of Chemical Research, 2007, 40, 1228-1236.
Baranyai et al., "Thermal Degradation of Ionic Liquids at Elevated Temperatures", Aust. J. Chem. 2004, 57, 145-147.

(Continued)

*Primary Examiner* — Michael M Bernshteyn
(74) *Attorney, Agent, or Firm* — Carolyn A. Fischer

(57) ABSTRACT

Presently described are polymerizable ionic liquids comprising a cation and an aromatic carboxylate anion; wherein the cation, anion, or both comprise a free-radically polymerizable group. Also described are curable compositions comprising such polymerizable ionic liquids and at least one other free-radically polymerizable monomer, oligomer, or polymer.

24 Claims, No Drawings

(56) References Cited

FOREIGN PATENT DOCUMENTS

| WO | WO 2007/030679 | 3/2007 |
|---|---|---|
| WO | WO 2007/030715 | 3/2007 |
| WO | WO 2008/021533 | 2/2008 |
| WO | WO 2009/134694 | 11/2009 |
| WO | WO 2011/025847 | 3/2011 |
| WO | WO 2011/025963 | 3/2011 |
| WO | WO 2011/031442 | 3/2011 |
| WO | WO 2011/087621 | 7/2011 |
| WO | WO 2011/146326 | 11/2011 |

OTHER PUBLICATIONS

Bowyer et al., "Indium-Mediated Addition of 4-Bromocrotonic Acid to Aldehydes and Ketones-A Simple, High Yielding Route to α-Allyl-β-Hydroxy Carboxylic Acids", Aust. J. Chem. 2004, 57, 135-137.
Castner, JR. et al., "Intermolecular Dynamics, Interactions, and Solvation in Ionic Liquids", Accounts of Chemical Research, 2007, 40, 1217-1227.
Earle et al., "Keto-Enol Tautomerism as a Polarity Indicator in Ionic Liquids", Aust. J. Chem. 2004, 57, 149-150.
Fainerman-Melnikova et al., "Metal-Ion Recognition-Selective Bulk Membrane Transport of Silver(I) Using Thioether Donor Macrocycles as Ionophores, and X-Ray Structure of the Silver Complex of an $S_4$-Donor Ring", Aust. J. Chem. 2004, 57, 161-166.
Forsyth et al., "Ionic Liquids Based on Imidazolium and Pyrrolidinium Salts of the Tricyanomethanide Anion", Aust. J. Chem. 2004, 57, 121-124.
Forsyth et al., "Ionic Liquids-An Overview", Aust. J. Chem. 2004, 57, 113-119.
Gou et al., "Measurement of the Dissolved Oxygen Concentration in Acryalte Monomers with a Novel Photochemical Methods", Journal of Polymer Science, Polym. Sci.: Part A: Polymer Chemistry. vol. 42, (2004), pp. 1285-1292.
Guest Editorial, "Ionic Liquids", Accounts of Chemical Research, 2007, 40, 1077-1078.
Han et al., "Ionic Liquids in Separations", Accounts of Chemical Research, 2007, 40, 1079-1086.
Hardcare et al., "Structure and Solvation in Ionic Liquids", Accounts of Chemical Research, 2007, 40, 1146-1155.
Hemeon et al., Manganese Dioxide Allylic and Benzylic Oxidation Reactions in Ionic Liquids, Aust. J. Chem. 2004, 57, 125-128.
Hu et al., "Room-Temperature Ionic Liquids: Slow Dynamics, Viscosity, and the Red Edge Effect", Accounts of Chemical Research, 2007, 40, 1097-1105.
Ilesinghe et al., "An Evaluation of Some Hindered Diamines as Chiral Modifiers of Metal-Promoted Reactions", Aust. J. Chem. 2004, 57, 167-176.
International Search Report PCT/US2011/036586 Jul. 22, 2011, 4pgs.
Iwata et al., "Local Structure Formation in Alkyl-imidazolium-Based Ionic Liquids as Revealed by Linear and Nonlinear Raman Spectroscopy", Accounts of Chemical Research, 2007, 40, 1174-1181.
Jimenez et al., "Frontal Polymerization with Monofunctional and Difunctional Ionic Liquid Monomers", Journal of Polymer Science: Part A: Polymer Chemistry, vol. 45, 2745-2754 (2007).
Jimenez et al., "Photopolymerization Kinetics of Ionic Liquid Monomers Derived From the Neutralization Reaction Between Trialkylamines and Acid-Containing (Meth)Acrylates", Journal of Polymer Science: Part A: Polyer Chemistry, pp. 3009-3021 (Dec. 2006/Feb. 2007).
Juger et al., "Synthesis, Polymerization and Conducting Properties of an Ionic Liquid-Type Anionic Monomer", Tatrahedron Letters 50 (2009) 128-131.
Klee et al., "Monomers for low shrinking composites, $2^a$—Synthesis of branched methacrylates and their application in dental composites," Macromolecular Chemistry and Physics, vol. 200, Issue 3, pp. 517-523, (1999).
Lu et al., "Advanced Applications of Ionic Liquids in Polymer Science", Progress in Polymer Science 34, (2009), 431-448.
Lynden-Bell et al., "Simulations of Ionic Liquids, Solutions, and Surfaces", Accounts of Chemical Research, 2007, 40, 1138-1145.
MacFarlane et al., "Ionic Liquids in Electrochemical Devices and Processes: Managing Interfacial Electrochemistry", Accounts of Chemical Research, 2007, 40, 1165-1173.
Maginn, "Atomistic Simulation of the Thermodynamic and Transport Properties of Ionic Liquids", Accounts of Chemical Research, 2007, 40, 1200-1207.
Nakajima, "Preparation of Termally Stable Polymer Electrolytes From Imidazolium-Type Ionic Liquid Derivatives", Science Direct, Polymer 46 (2005) 11499-11504.
Ohno et al., "Amino Acid Ionic Liquids", Accounts of Chemical Research 2007, 40, 1122-1129.
Ohno et al., "Development of new class of ion conductive polymers based on ionic liquids", Electrochimica ACTA, vol. 50, No. 2-3, Nov. 30, 2004, pp. 254-260.
Olivier-Bourbigou et al.; "Ionic Liquids and Catalysis: Recent Progress From Knowledge to Applications", Applied Catalysis A: General 373 (2010) 1-56.
Padua et al., Molecular Solutes in Ionic Liquids: A Structural Perspective, Accounts of Chemical Research, 2007, 40, 1087-1096.
Plechkova et al., "Applications of ionic liquids in the chemical industry", Chemical Society Reviews, 2008, 37, pp. 123-150.
Popolo et al., "Clusters, Liquids and Crystals of Dialkyimidazolium Salts. A Combined Perspective from ab Initio and Classical Computer Simulations", Accounts of Chemical Research, 2007, 40, 1156-1164.
Rebelo et al., "Accounting for the Unique Double Dual Nature of Ionic Liquids from a Molecular Thermodynamic and Modeling Standpoint", Accounts of Chemical Research, 2007, 40, 1114-1121.
Shim et al., "Solvation, Solute Rotation and Vibration Relaxation, and Electrom-Transfer Reactions in Room-Temperature Ionic Liquids", Accounts of Chemical Research 2007, 40, 1130-1137.
Smiglak et al., "The Second Evolution of Ionic Liquids: From Solvents and Separations to Advanced Materials-Energetic Examples From the Ionic Liquid Cookbook", Accounts of Chemical Research 2007, 40, 1182-1192.
Soulivong et al., "A Long-Chain Phosphine Designed as a Metal-lomesogen Generator-Synthesis and Coordination Properties", Aust. J. Chem. 2004, 57, 157-160.
Torimoto et al., "New Frontiers in Materials Science Opened by Ionic Liquids", Adv. Mater. 2009, 21, 1-26.
Vijayaraghavan et al., "Charge Transfer Polymerization in Ionic Liquids", Aust. J. Chem. 2004, 57, 129-133.
Wang et al., "Understanding Ionic Liquids through Atomistic and Coarse-Grained Molecular Dynamics Simulations", Accounts of Chemical Research, 2007, 40, 1193-1199.
Whitehead et al., "Analysis of Gold in Solutions Containing Ionic Liquids by Inductively Coupled Plasma Atomic Emission Spectrometry", Aust. J. Chem. 2004, 57, 151-155.
Yoshizawa et al., "Design of Ionic Liquids for Electrochemical Applications", Aust. J. Chem. 2004, 57, 139-144.
Yoshizawa et al., "Novel Polymer Electrolytes Prepared by Copolymerization of Ionic Liquid Monomers", Polymers for Advanced Technologies 13, 589-594 (2002).

\* cited by examiner

POLYMERIZABLE IONIC LIQUID COMPRISING AROMATIC CARBOXYLATE ANION

CROSS REFERENCE TO RELATED APPLICATIONS

This is a national stage filing under 35 U.S.C. 371 of PCT/US2011/036586, filed May 16, 2011, which claims priority to U.S. Provisional Application Nos. 61/345,624, filed May 18, 2010, and 61/360,139, filed Jun. 30, 2010, and the disclosure of which is incorporated by reference in their entirety herein.

BACKGROUND

Ionic liquids (ILs) are salts in which the cation and anion are poorly coordinated. At least one of the ionic components is organic and one of the ions has a delocalized charge. This prevents the formation of a stable crystal lattice, and results in such materials existing as liquids, often at room temperature, and at least, by definition, at less than 100° C. For example, sodium chloride, a typical ionic salt, has a melting point of about 800° C., whereas the ionic liquid N-methylimidazolium chloride has a melting point of about 75° C.

Ionic liquids typically comprise an organic cation, such as a substituted ammonium or a nitrogen-containing heterocycle, such as a substituted imidazolium, coupled with an inorganic anion. However, species have also been described wherein the cation and anion are organic. When the ionic liquid comprises at least one polymerizable group, such ionic liquid is a polymerizable ionic liquid ("PIL").

SUMMARY

Presently described are polymerizable ionic liquids comprising a cation and an aromatic carboxylate anion; wherein the cation, anion, or both comprise a free-radically polymerizable group.

In some embodiments, the cation comprises a free-radically polymerizable group and the anion lacks a free-radically polymerizable group.

In other embodiments, the anion comprises a free-radically polymerizable group and the cation lacks a free-radically polymerizable group.

In yet other embodiments, the anion and cation each comprise at least one free-radically polymerizable group.

In some favored embodiments, the cation is a substituted ammonium, phosphonium, or imidazolium cation.

DETAILED DESCRIPTION

As used herein:

"hardenable" is descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

"hardened" refers to a material or composition that has been cured (e.g., polymerized or crosslinked).

"(meth)acrylate" is a shorthand reference to acrylate, methacrylate, or combinations thereof "(meth)acrylic" is a shorthand reference to acrylic, methacrylic, or combinations thereof and "(meth)acryl" is a shorthand reference to acryl, methacryl, or combinations thereof.

"alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent.

"aromatic group" or "aromatic moiety" includes 6-18 ring atoms and can contain optional fused rings, which may be saturated or unsaturated. Examples of aromatic groups include phenyl, naphthyl, biphenyl, phenanthryl, and anthracyl. The aromatic group may optionally contain 1-3 heteroatoms such as nitrogen, oxygen, or sulfur and can contain fused rings. Examples of aromatic group having heteroatoms include pyridyl, furanyl, pyrrolyl, thienyl, thiazolyl, oxazolyl, imidazolyl, indolyl, benzofuranyl, and benzthiazolyl. Unless otherwise noted the aromatic group may be mono- or polyvalent.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

Presently described are various curable compositions that comprise a polymerizable ionic liquid, comprising a cation and anion that are poorly coordinated. Such polymerizable ionic liquids have a melting point ($T_m$) below about 100° C. The melting point of these compounds is more preferably below about 60° C., 50° C., 40° C., or 30° C. and most preferably below about 25° C., for ease of use in various polymerizable compositions as described herein with or without the aid of solvent carriers in the composition. Polymerizable ionic liquids having a melting point below 25° C. are liquids at ambient temperature. As the molecular weight of the polymerizable ionic liquid increases, the viscosity can increase. In some embodiments, the molecular weight of the polymerizable ionic liquid is less than 1000 g/mole.

Suitable cationic groups, also known as onium salts, include substituted ammonium salts, substituted phosphonium salts, substituted pyridinium salts, and substituted imidazolium salts. The structures of the cations of such onium salts are depicted as follows:

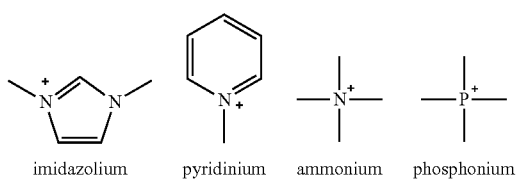

imidazolium    pyridinium    ammonium    phosphonium

Other cationic groups include pyrazolium, pyrrolidinium, and cholinium.

Presently described are ionic liquids comprising a cation and an aromatic carboxylate anion. "Aromatic carboxylate anion" refers to a carboxylate anion bonded directly or indirectly via a linking group (L) to an aromatic moiety (Ar). The anion is organic and typically monovalent anion, i.e. having a charge of −1. The aromatic carboxylate anion may be depicted by the following formulas $^-$O(CO)Ar or $^-$O(CO)-L-Ar.

The cation, the anion, or a combination thereof further comprises a polymerizable group. The polymerizable groups are typically ethylenically unsaturated (e.g. terminal) groups. The ethylenically unsaturated groups are preferably free-radically polymerizable group. Such free-radically polymerizable groups include (meth)acryl groups such as (meth)acrylamide ($H_2C$=CHCON— and $H_2C$=CH($CH_3$)CON—) and (meth)acrylate($CH_2$CHCOO— and $CH_2C(CH_3)$COO—). Other free-radically polymerizable groups include vinyl ($H_2C$=C—) including vinyl ethers ($H_2C$=CHOCH—).

The methacrylate functional onium salts are typically preferred for some uses such as hardenable dental compositions over the acrylate onium salts in compositions because they exhibit a slower rate of cure. However, for other uses wherein faster cure rate are desired, acrylate groups are favored over (meth)acrylate groups.

In some embodiments, the cation comprises a (e.g. free-radically) polymerizable group (P) and the anion lacks a (e.g. free-radically) polymerizable group and thus is a non-polymerizable anion.

In other embodiments, the organic anion comprises a (e.g. free-radically) polymerizable group, and the cation lacks a (e.g. free-radically) polymerizable group and thus is a non-polymerizable cation. When the anion comprises a (e.g. free-radically) polymerizable group the anion may be depicted by the following formulas $^-$O(CO)ArP or $^-$O(CO)-L-ArP, $^-$O(CO)Ar-L-P, or $^-$O(CO)-L-Ar-L-P; wherein L is a (e.g. divalent) linking group. Depending on the synthesis employed, such linking group may comprise an ester linkage, amide linkage, urea linkage, urethane linkage, ether linkage or carbonate linkage.

In yet other favored embodiments, both the anion and the cation each comprise a (e.g. free-radically) polymerizable group. Thus, the (e.g. free-radically) polymerizable ionic liquid can be describes as a multifunctional or difunctional (e.g. free-radically) polymerizable ionic liquid. In favored embodiments, the free-radically polymerizable ionic liquid can be described as a multi(meth)acrylate or di(meth)acrylate polymerizable ionic liquid.

In some embodiments, the (e.g. free-radically) polymerizable ionic liquid described herein comprises a substituted ammonium cation.

Such (e.g. free-radically) polymerizable ionic liquids may have the general formula:

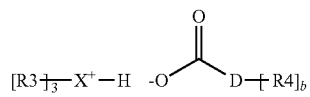

Wherein

X is nitrogen or phosphorus;

R3 and R4 are independently alkyl or heteroalkyl, and at least one R3 or R4 comprises a free-radically polymerizable group;

D comprises an aromatic moiety and optionally comprises a linking group between the carboxylate end group and aromatic moiety and/or optionally comprises a linking group between the aromatic moiety and R4; and b is 0-2.

The free-radically polymerizable groups are preferably (meth)acrylate groups. The aromatic moiety of D typically comprises one, two, or three aromatic rings that are optionally fused, such as in the case of phthalate or aromatic rings derived from biphenyl or triphenyl compounds.

In some embodiments, the substituted ammonium cation lacks (e.g. free radically) polymerizable groups such as (meth)acrylate groups. The ammonium cation may comprise heteroalkyl and more commonly alkyl substituents, such as alkyl groups having at least one carbon atom (e.g. methyl) and typically no greater than 8, or no greater than 6, or no greater than 4 carbon atoms. In this embodiment, the anion comprises a (e.g. free radically) polymerizable groups such as (meth)acrylate group. In some embodiments, D may comprise an a divalent (e.g. ester) linking group between a (e.g. phenyl) aromatic group and terminal (meth)acrylate group.

Examples of such free-radically polymerizable ionic liquids include:

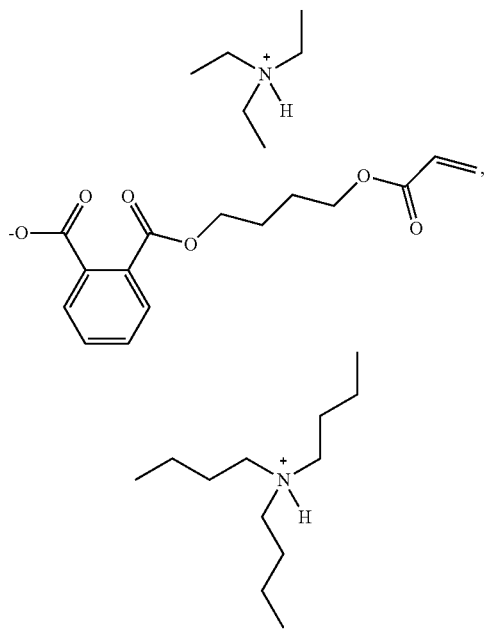

-continued

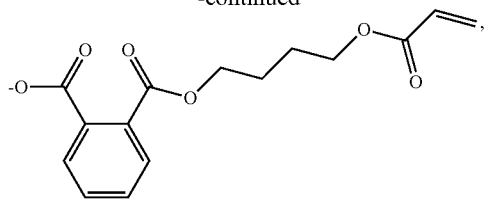

and

In another embodiment, the substituted ammonium cation comprises at least one (e.g. free-radically) polymerizable groups, such as (meth)acrylate group. A linking group is typically present between the terminal (e.g. free-radically) polymerizable (meth)acrylate group and the (e.g. ammonium) cation ($X^+$). Such linking group may comprise an ester linkage, amide linkage, urea linkage, urethane linkage, ether linkage or carbonate linkage, depending on the synthesis employed. In some embodiments, two R3 are alkyl groups and one R3 group comprises a (meth)acrylate group. The alkyl groups of R3 typically comprise at least one carbon atom (e.g. methyl) and no greater than 8, or no greater than 6, or no greater than 4 carbon atoms. When the cation comprises one or more free radically polymerizable groups, the anion may lack (e.g. free-radically) polymerizable groups. In this embodiment, R4 may comprise heteroalkyl and more commonly alkyl substituents, such as those having at least one carbon atom (e.g. methyl) and typically no greater than 8, or no greater than 6, or no greater than 4 carbon atoms.

Examples of such free-radically polymerizable ionic liquids include:

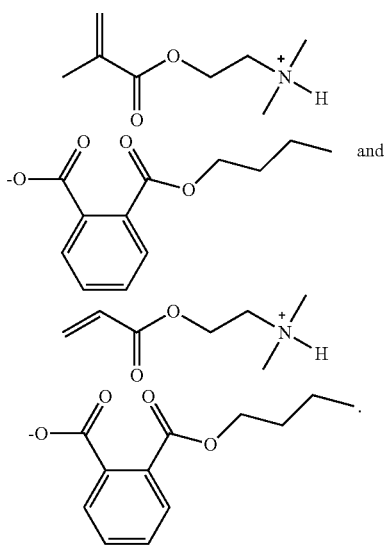

In yet another embodiment, both the substituted ammonium cation and the aromatic carboxylate anion each comprise at least one free radically polymerizable group, such as (meth)acrylate groups. In some embodiments, two R3 are alkyl groups and one R3 group comprises a (meth)acrylate group. In another embodiment, two R3 are alkyl groups and one R3 group comprises an aromatic (e.g. phenyl) (meth)acrylate group. The alkyl groups of R3 typically comprise at least one carbon atom (e.g. methyl) and no greater than 8, or no greater than 6, or no greater than 4 carbon atoms. A linking group is typically present between the terminal (e.g. free-radically) polymerizable (meth)acrylate group and the (e.g. ammonium) cation ($X^+$), a previously described. D may comprise a divalent (e.g. ester) linking group between a (e.g. phenyl) aromatic group and terminal (meth)acrylate group.

Examples of such free-radically polymerizable ionic liquids include:

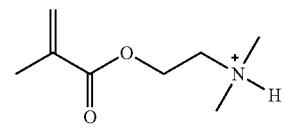

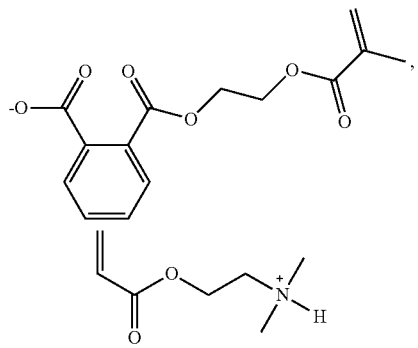

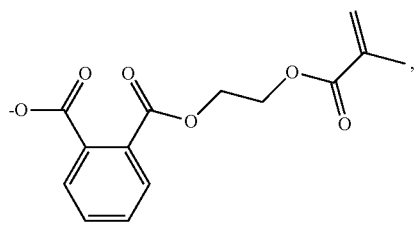

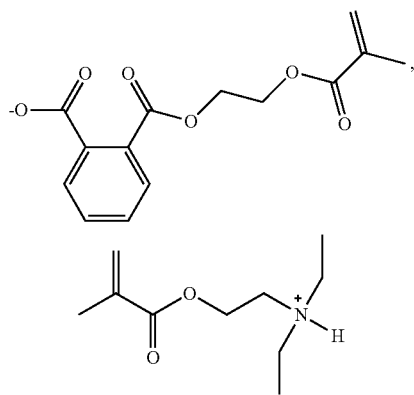

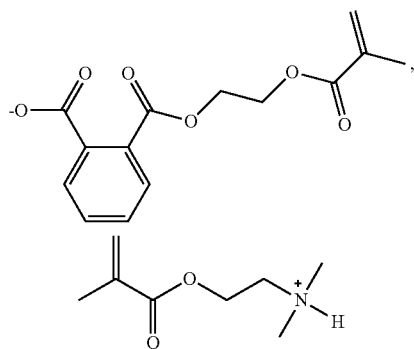

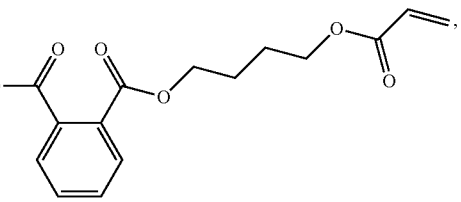

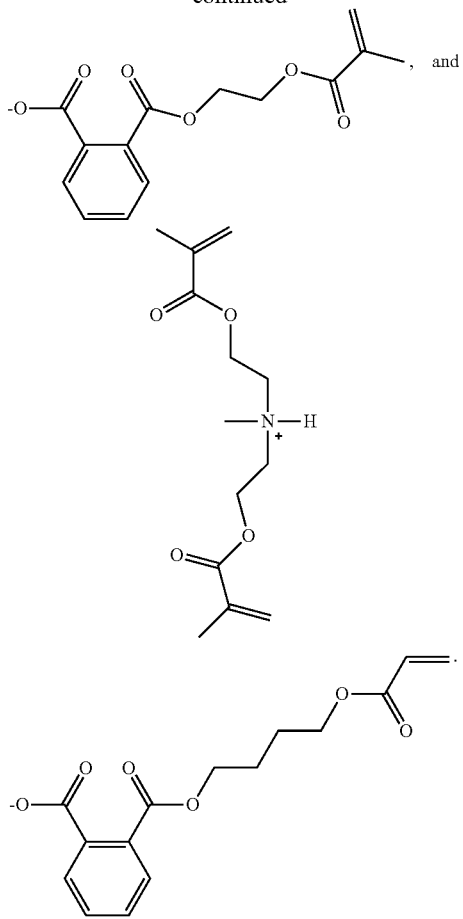

In other embodiments, the (e.g. free-radically) polymerizable ionic liquid described herein comprises a substituted imidazolium cation.

The (e.g. free-radically) polymerizable ionic liquid may have the general formula:

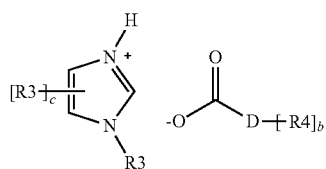

wherein
R3 and R4 are independently alkyl or heteroalkyl, and at least one R3 or R4 comprises a free-radically polymerizable group;
D comprises an aromatic moiety and optionally comprises a linking group between the carboxylate end group and aromatic moiety and/or optionally comprises a linking group between the aromatic moiety and R4;
c is 0 to 3; and
b is 0-2.

The free-radically polymerizable groups are preferably (meth)acrylate groups. The aromatic moiety of D typically comprises one, two, or three aromatic rings that are optionally fused, such as in the case of phthalate or aromatic rings derived from biphenyl or triphenyl compounds.

In some embodiments, the substituted imidazolium cation lacks (e.g. free radically) polymerizable groups such as (meth)acrylate groups. The imidazolium may comprise heteroalkyl and more alkyl commonly substituents, such as those having 1 to 4, 5, 6, 7, or 8 carbon atoms. In this embodiment, the anion comprises a (e.g. free radically) polymerizable groups such as (meth)acrylate group. In one embodiment, R4 comprises a divalent (e.g. ester) linking group between a (e.g. phenyl or biphenyl) aromatic group and a terminal (meth)acrylate group.

Illustrative species include:

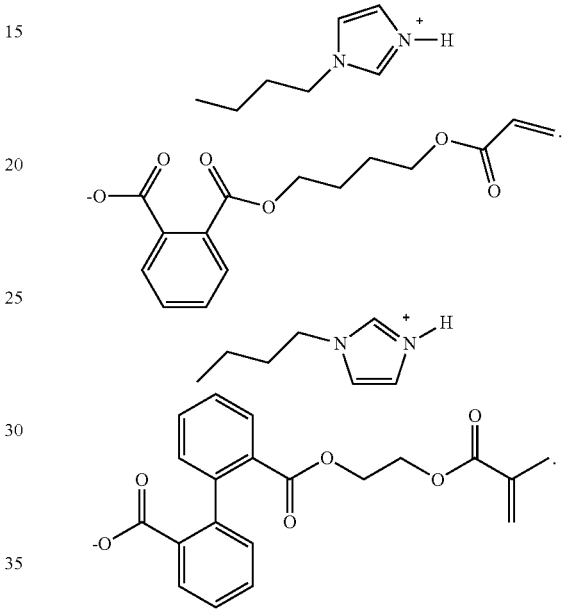

In another embodiment, the substituted imidazolium cation may comprise at least one (e.g. free-radically) polymerizable groups such as (meth)acrylate group. When the cation comprises at least one free-radically polymerizable group, such as a (meth)acrylate group, the anion may lack free-radically polymerizable groups. A linking group is typically present between the terminal (e.g. free-radically) polymerizable (meth)acrylate group and the imidazolium cation. Such linking group may comprise an ester linkage, amide linkage, urea linkage, urethane linkage, ether linkage or carbonate linkage, depending on the synthesis employed.

In yet another embodiments, both the substituted imidazolium cation and the aromatic carboxylate anion comprise at least one free-radically polymerizable groups such as (meth)acrylate group. A linking group is typically present between the terminal (e.g. free-radically) polymerizable (meth)acrylate group and the imidazolium cation, as just described.

Examples of such free-radically polymerizable ionic liquids include:

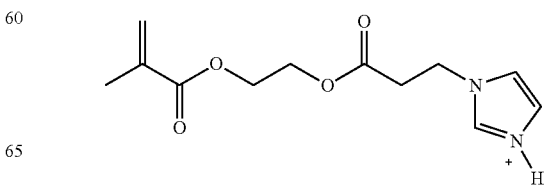

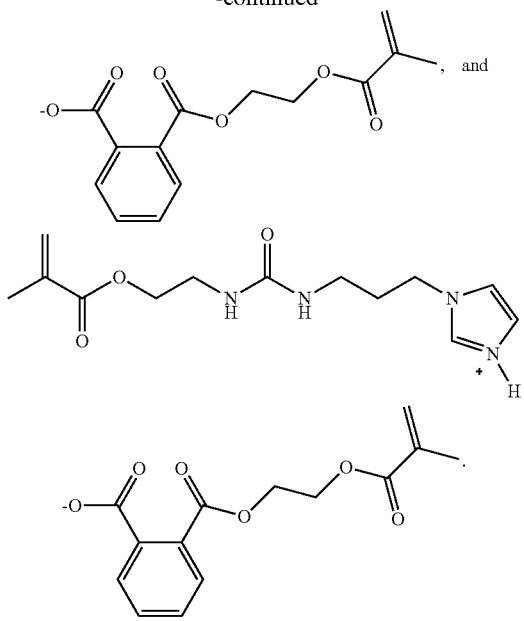

The (e.g. free-radically) polymerizable ionic liquids described herein can be made by several methods.

The simplest method is the mixing of an equimolar amount of a (e.g. commercially available) tertiary amine and a carboxylic acid wherein at least one of the components contains a (e.g. free radically) polymerizable group and the carboxylic acid contains an aromatic group. The free radically polymerizable group(s) is not reacted during the formation of the ionic liquid and thus is present on the formed compound.

Useful tertiary amines include alkyl or aryl amines such as triethylamine, tripropyl amine, tributylamine, dimethyl isopropylamine, dimethylhexylamine, dimethyl cylochexylamine, 1-methylpyrrolidine, 1-methylpiperidine, 4-methylmorpholine, dimethyl aniline, triphenylamine, dimethyl benzylamine, and N-methyldiphenylamine. Other useful amines include heterocyclic amines such as 1-methyl imidazole, 1-butyl imidazole, 1-methylpyrrole, 1-methyl indole, 9-methyl carbazole, and pyridine. Further useful amines include polymerizable tertiary amines, such as 1-vinyl imidazole and N,N-dialkyl amino ethyl(meth)acrylates, such as N,N-dimethyl aminoethyl(meth)acrylate, N,N-diethyl aminoethyl(meth)acrylate, and N,N-diisopropyl aminoethyl (meth)acrylate.

Useful carboxylic acids, that lack free-radically polymerizable groups, include benzoic acid, alkyl benzoic acids, such as toluic acid, ethyl benzoic acid, butyl benzoic acid and dimethyl benzoic acid; bromobenzoic acid, chlorobenzoic acid, alkyloxy benzoic acids such as anisic acid; mono-phthalate esters, such as mono-butyl phthalate; biphenyl benzoic acid, phenoxybenzoic acid, napthoic acid, fluorine carboxylic acid, and fluorenone carboxylic acid. Other useful non-polymerizable acids include phenyl acetic acid, triphenyl acetic acid, 2-phenyl propionic acid, hydrocinnamic acid, alpha-methylhydrocinnamic acid, 3,3-diphenylpropionic acid, 4-phenylbutyric acid, 5-phenylvaleric acid, 6-phenylhexanoic acid, phenoxyacetic acid, 3-phenoxypropionic acid, tolylacetic acid, 4-methoxyphenyl acetic acid, 4-biphenyl acetic acid, trans cinnamic acid, and 4-methyl cinnamic acid. Such carboxylic acids provide anions that lack free-radically polymerizable groups.

Useful carboxylic acids, that comprise free-radically polymerizable groups, include (meth)acrylic functional mono esters of phthalic acid, isophthalic acid, terephthalic acid, diphenic acid, biphenyl dicarboxylic acid, and naphthalene dicarboxylic acid. Specific examples of these compounds include mono-2-(methacryloxy)ethyl phthalate, mono-2-(acryloxy)butyl phthalate, and biphenyl-2,2'-dicarboxylic acid 2-[2-(2-methyl-acryloyloxy)-ethyl]ester. Such carboxylic acids provide anions comprising free-radically polymerizable groups.

Another method includes the reaction of an amine or hydroxyl functional tertiary amine precursor with a (e.g. free-radically) polymerizable isocyanate (or a polymerizable acid or anhydride, such as methacrylic anhydride), followed by neutralization with a carboxylic acid, such as depicted by the following reaction scheme:

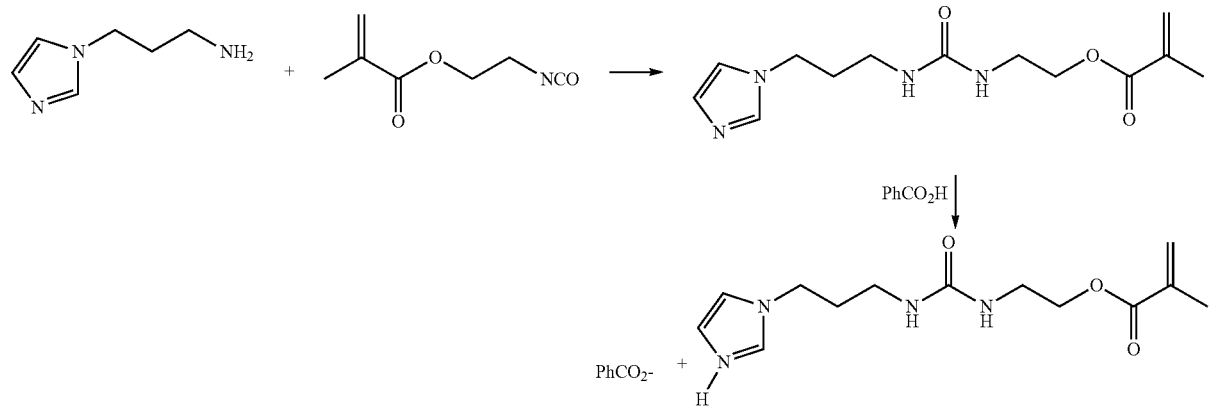

Commercially available starting materials include aminopropyl imidazole, N,N-dimethylethylene diamine, N,N-diethylethylenediamine, N,N-dibutylethylenediamine, N,N,N'-trimethylethylenediamine, N,N-dimethyl-N'-ethylethylenediamine, 3-dimethylaminopropylamine, 3-diethylaminopropylamine, 1-(2-aminoethyl)piperidine, 1-methylpiperizine, 3-aminopropyl morpholine, N,N-dimethylethanolamine, N,N-diethylethanolamine, 2-(diisopropylamino)ethanol, 3-dimethylamino-1-propanol, 1-dimethylamino-2-propanol, 1-(2-hydroxyethyl)pyrrolidine, 1-piperidine ethanol, 4-(2-hydroxyethyl)morpholine, diethanol amine, diisopropanol amine, N-methyldiethanol amine, N-ethyldiethanol amine, N-butyldiethanol amine, triethanol amine, 1-[N,N-bis(2-hydroxyethyl)-amino]-2-propanol, triisopropanol amine, 3-amino-1,2-propanediol, 3-(dimethylamino)-1,2-propanediol, 3-(diethylamino)-1,2-propanediol, 3-(dipropylamino)-1,2-propanediol, 3-(diisopropylamino)1,2-propanediol, 2-amino-1,3-propanediol, 2-amino-2-ethyl-1,3-propanediol, 2-amino-2-methyl-1,3-propanediol, tris(hydroxymethyl)amino methane, bis(2-hydroxyethyl)amino-tris(hydroxymethyl)methane, 2,2-bis(hydroxymethyl)-2,2',2''-nitrilotriethanol, N,N' bis(2-hydroxyethyl)-ethylenediamine, N—N—N'—N'-tetrakis(2-hydroxypropyl)-ethylenediamine, 1,3-bis[tris(hydroxymethyl)-methylamino]propane, 3-pyrrolidino-1,2-propanediol, 3-piperidino-1,2-propanediol, and 1,4-bis(2-hydroxyethyl)-piperazine.

Useful carboxylic acids include the same compounds described for the simple mixing method.

Another method includes the reaction of an amine with an acrylate compound to provide a (e.g. free-radically) polymerizable amine precursor, followed by neutralization, such as depicted by the following reaction scheme:

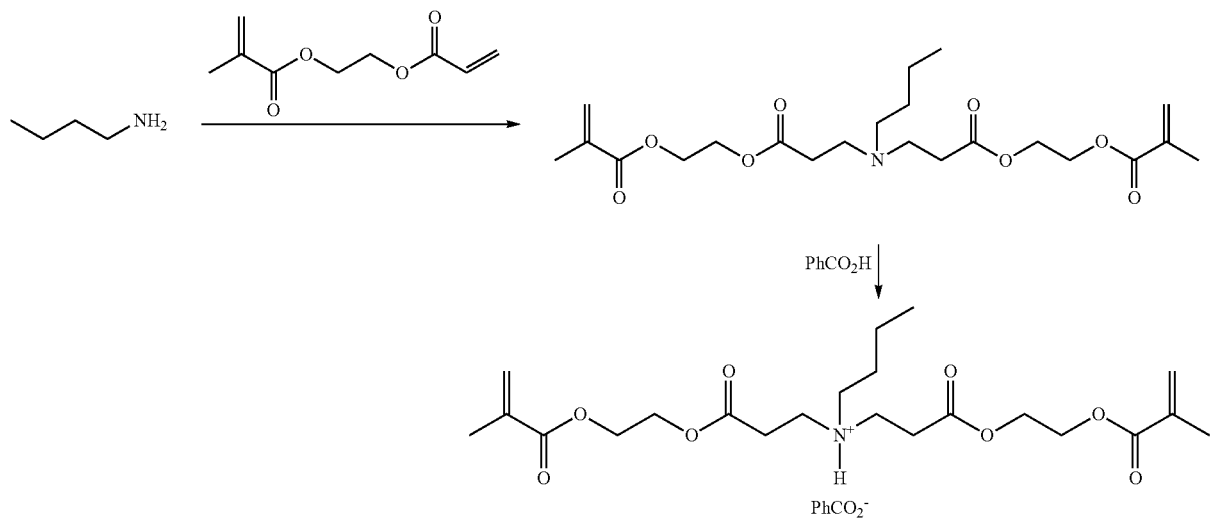

Commercially available starting materials include amines such as methylamine, ethylamine, propylamine, butylamine, hexylamine, isopropylamine, isobutylamine, 1-methylbutylamine, 1-ethy propylamine, 2-methylbutylamine, isoamylamine, 1,2-dimethylpropylamine, 1,3-dimethylbutylamine, 3,3-dimethylbutylamine, 2-aminoheptane, 3-aminoheptane, 1-methylheptyamine, 2-ethylhexylamine, 1,5-dimethylhexylamine, cyclopropylamine, cyclohexylamine, cyclobutylamine, cyclopentylamine, cycloheptylamine, cyclooctylamine, 2-aminonorbornane, 1-adamantanamine, allylamine, tetrahydrofurfurylamine, ethanolamine, 3-amino-1-propanol, 2-(2-aminoethoxy)ethanol, benzylamine, phenethylamine, 3-phenyl-1-propylamine, 1-aminoindan, ethylenediamine, diaminopropane, and hexamethylenediamine.

Another method includes the reaction of an aromatic anhydride precursor with a hydroxyl functional (meth)acrylate precursor in the presence of a tertiary amine to form the (e.g. free-radically) polymerizable ionic liquid in a one step reaction, such as depicted in the following scheme:

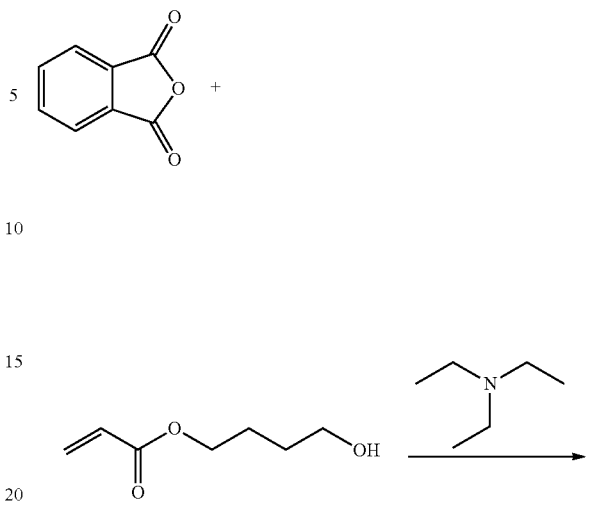

-continued

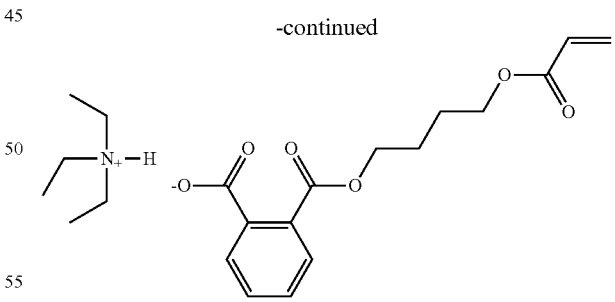

Useful aromatic anhydrides include phthalic anhydride, 4-methyl phthalic anhydride, diphenic anhydride, 1,8-naphthalic anhydride, 2-phenylglutaric anhydride, homophthlic anhydride, phenyl succinic anhydride, phenyl maleic anhydride, 2,3-diphenyl maleic anhydride, and benzene tetracarboxylic dianhydride.

Useful hydroxyl functional (meth)acrylates include 2-hydroxyethyl(meth)acrylate, hydroxylpropyl(meth)acrylate, and hydroxybutyl(meth)acrylate.

Useful tertiary amines include those previously described.

In yet another method, imidazole compounds may be prepared by the Michael addition reaction of an imidazole compound to a poly(meth)acryloyl compound as described in U.S. Provisional Application Ser. No. 61/345,624, filed May 18, 2010, titled, "POLYMERIZABLE IONIC LIQUID COMPOSITIONS"; incorporated herein by reference.

The (e.g. free-radically) polymerizable ionic liquid functions as a reactive monomer and thus is substantially unpolymerized in the curable composition at the time the curable composition is applied to a substrate or formed into a (e.g. dental) article, such as a dental crown. Hence, the curable composition hardens upon curing via polymerization of the (e.g. free-radically) ethylenically unsaturated groups of the (e.g. multifunctional) polymerizable ionic liquid. Such curing generally results in a permanent bond.

In some favored embodiments, the (e.g. free-radically) polymerizable ionic liquid is sufficiently low in viscosity that it acts as a reactive diluent. In such embodiment, the composition can advantageously be substantially free of solvents, especially organic solvents. This can result in increased efficiency with respect to manufacturing time as well as energy consumption by reducing or eliminating drying the composition prior to curing. This can also reduce the volatile organic content (VOC) emissions of the composition.

In some embodiments, the (e.g. free-radically) polymerizable ionic liquid is monofunctional, having one (e.g. free-radically) polymerizable ethylenically unsaturated group. Monofunctional polymerizable ionic liquids can be combined with conventional multifunctional ethylenically unsaturated (e.g. (meth)acrylate) monomers to enhance curing thereby minimizing the formation of a surface residue surmised to be caused by oxygen curing inhibition of curable compositions.

In other embodiments, the (e.g. free-radically) polymerizable ionic liquid is multifunctional, typically comprising two or three (e.g. free-radically) polymerizable groups. For example, in some embodiments the (e.g. free-radically) polymerizable ionic liquid may comprise a (e.g. free-radically) polymerizable cation and a (e.g. free-radically) polymerizable anion. In other embodiments, the multifunctional polymerizable ionic liquids described herein can be characterized as having a multifunctional (e.g. substituted ammonium) cation, having two, three, or more (e.g. free-radically) polymerizable groups bonded to the same cationic group.

In some embodiments, the (e.g. free-radically) polymerizable ionic liquid is a mixture comprising at least one multifunctional polymerizable ionic liquid and at least one monofunctional polymerizable ionic liquid.

The (e.g. free-radically) polymerizable ionic liquid(s) is typically employed in combination with other conventional (e.g. (meth)acrylate) free-radically polymerizable monomer(s), oligomer(s), or polymer(s). By "other" is it meant an ethylenically unsaturated monomer that is not a (e.g. free-radically) polymerizable ionic liquid. Although conventional monomers are polymerizable and many are liquids at 25° C., conventional monomers are typically nonionic, lacking a cation and an anion.

It has been found that a (e.g. free-radically) polymerizable ionic liquid can be used in place of conventional hardenable (meth)acrylate monomers, such as 2-hydroxylethyl methacrylate (HEMA), triethyleneglycol dimethacrylate (TEGDMA), and 2,2-bis[4-(2-hydroxy-3-methacyloxypropoxy)phenyl]propane (BisGMA), such as commonly used in curable (e.g. dental) compositions. Such embodiment is amenable to providing a polymerizable (e.g. dental) composition that is free of monomer derived from bisphenol A (such as BisGMA).

Preferred (e.g. multifunctional) polymerizable ionic liquids exhibit a high air to nitrogen curing exotherm ratio, as can be measured by photo DSC according to the test method described in the examples. The air to nitrogen curing ratio is typically at least 0.70 or 0.75. In preferred embodiments, the air to nitrogen curing exotherm ratio is typically at least the 0.80, 0.85, 0.90, or 0.95. For embodiments wherein the air to nitrogen curing ratio of the polymerizable ionic liquid is sufficiently high, the polymerizable ionic liquid can advantageously be substantially completely cured in air (i.e. an oxygen rich environment) rather than requiring curing in the absence of oxygen.

A completely cured (i.e. hardened) polymerizable ionic liquid is solid at 25° C. and is substantially free of uncured polymerizable ionic liquid. When significant uncured polymerizable ionic liquid is present it typically results as a surface residue exhibiting a "wet" appearance. Minimal surface inhibition not only provides more complete curing but also minimizes the formation of a less cured oxygen inhibited surface layer. This provides the benefit of reduced extractables and also less need to remove the uncured "wet" monomer layer by use of an absorbant wiping material with or without a solvent such as ethanol. The extent of curing can be determined by various methods known in art. One common method is to determine the amount of uncured material by solvent extraction. In preferred embodiments, the amount of uncured extractable polymerizable ionic liquid is less than 10%, more preferably less than 5%, and most preferably less than 1% by weight of the cured composition.

Conventional (meth)acrylate monomers typically have an air to nitrogen curing exotherm ratio of no greater than 0.50, 0.40, 0.35, 0.20, or 0.25 or lower. For example, TEGMA has been found to have an air to nitrogen curing exotherm ratio of about 0.36; whereas HEMA has been found to have an air to nitrogen curing exotherm ratio of less than 0.25. Although the photocuring of conventional (meth)acrylate monomers and especially methacrylate monomers is typically inhibited by oxygen present in air, the inclusion of the (e.g. multifunctional) polymerizable ionic liquid can sufficiently increase the air to nitrogen curing exotherm of the mixture such that the mixture can advantageously be substantially completely cured in air. For embodiments wherein the composition is to be cured in air and the multifunctional polymerizable ionic liquid is combined with another polymerizable (meth)acrylate component that exhibits a lower air to nitrogen curing exotherm ratio, the air to oxygen curing exotherm ratio of the (e.g. multifunctional) polymerizable ionic liquid, described herein, is preferably at least 0.85, 0.90, or 0.95.

The total concentration of (e.g. multifunctional) polymerizable ionic liquid(s) having a high air to nitrogen curing exotherm ratio, is typically at least 30 wt-% and preferably at least 40 wt-% of the unfilled composition (the total polymerizable organic composition excluding inorganic filler). In this embodiment, the total concentration of other ethylenically unsaturated (e.g. (meth)acrylate) monomer(s), oligomer(s), and polymer(s)) is typically at least 10 wt-%, 20 wt-%, 30 wt-%, 40 wt-%, 50 wt-%, or 65 wt-%.

Although the presence of the (e.g. multifunctional) polymerizable ionic liquid having a high air to oxygen curing ratio is beneficial to curing, as just described, the presence of the other conventional (meth)acrylate monomer may also benefit the (e.g. multifunctional) polymerizable ionic liquid by improving the stability by hindering unintended polymerization, such as during storage, prior to (e.g. photo) curing. This is amenable to providing one-part curable coating composition. Thus, in at least some favored embodiments the amount of other ethylenically unsaturated (e.g. (meth)acrylate)

monomer(s), oligomer(s) is typically at least 21 wt-%, 22 wt-%, 23 wt-%, 24 wt-%, or 25 wt-% of the unfilled composition. Thus, the concentration of (e.g. multifunctional) polymerizable ionic liquid(s) having a high air to oxygen curing ratio is less than 80 wt-%. Typically, it is preferred to maximize the concentration of other ethylenically unsaturated (e.g. (meth)acrylate) monomer(s), oligomer(s) provided that the air to oxygen curing ratio of the mixture is at least 0.75 and preferably at least 0.80, 0.85, 0.90 or greater. Depending on the selection of other ethylenically unsaturated (e.g. (meth) acrylate) monomer(s), oligomer(s), this concurrent can be achieved with when the concentration of (e.g. multifunctional) polymerizable ionic liquid(s) having a high air to oxygen curing ratio is at least about 35 wt-%, 40 wt-%, or 45 wt-%. For embodiments, wherein the other ethylenically unsaturated monomer(s), oligomer(s), and polymer(s) has an air to oxygen curing exotherm of about 0.25 or lower, the concentration of polymerizable ionic liquid is preferably at least 50 wt-%, 55 wt-%, or 60 wt-%.

In addition to the polymerizable ionic liquids described herein, the curable component of the composition can include a wide variety of other ethylenically unsaturated compounds (with or without acid functionality), epoxy-functional (meth) acrylate resins, vinyl ethers, and the like.

The (e.g., photopolymerizable) compositions may include compounds having free radically reactive functional groups that may include monomers, oligomers, and polymers having one or more ethylenically unsaturated group. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-, di- or poly-(meth)acrylates (i.e., acrylates and methacrylates).

Some illustrative examples of other polymerizable monomers, oligomers, or polymers useful herein include, for example, poly(meth)acryl monomers selected from the group consisting of (a) mono(methacryl) containing compounds such as phenoxyethyl acrylate, ethoxylated phenoxyethyl acrylate, 2-ethoxyethoxyethyl acrylate, ethoxylated tetrahydrofurfural acrylate, and caprolactone acrylate, (b) di(meth) acryl containing compounds such as 1,3-butylene glycol diacrylate, 1,4-butanediol diacrylate, 1,6-hexanediol diacrylate, 1,6-hexanediol monoacrylate monomethacrylate, ethylene glycol diacrylate, alkoxylated aliphatic diacrylate, alkoxylated cyclohexane dimethanol diacrylate, alkoxylated hexanediol diacrylate, alkoxylated neopentyl glycol diacrylate, caprolactone modified neopentylglycol hydroxypivalate diacrylate, caprolactone modified neopentylglycol hydroxypivalate diacrylate, cyclohexanedimethanol diacrylate, diethylene glycol diacrylate, dipropylene glycol diacrylate, ethoxylated (10) bisphenol A diacrylate, ethoxylated (3) bisphenol A diacrylate, ethoxylated (30) bisphenol A diacrylate, ethoxylated (4) bisphenol A diacrylate, hydroxypivalaldehyde modified trimethylolpropane diacrylate, neopentyl glycol diacrylate, polyethylene glycol (200) diacrylate, polyethylene glycol (400) diacrylate, polyethylene glycol (600) diacrylate, propoxylated neopentyl glycol diacrylate, tetraethylene glycol diacrylate, tricyclodecanedimethanol diacrylate, triethylene glycol diacrylate, tripropylene glycol diacrylate; (c) tri(meth)acryl containing compounds such as glycerol triacrylate, trimethylolpropane triacrylate, pentaerythritol triacrylate, ethoxylated triacrylates (e.g., ethoxylated (3) trimethylolpropane triacrylate, ethoxylated (6) trimethylolpropane triacrylate, ethoxylated (9) trimethylolpropane triacrylate, ethoxylated (20) trimethylolpropane triacrylate, propoxylated triacrylates (e.g., propoxylated (3) glyceryl triacrylate, propoxylated (5.5) glyceryl triacrylate, propoxylated (3) trimethylolpropane triacrylate, propoxylated (6) trimethylolpropane triacrylate), tris(2-hydroxyethyl)isocyanurate triacrylate; (d) higher functionality (meth)acryl containing compounds such as pentaerythritol tetraacrylate, ditrimethylolpropane tetraacrylate, dipentaerythritol pentaacrylate, ethoxylated (4) pentaerythritol tetraacrylate, caprolactone modified dipentaerythritol hexaacrylate; (e) oligomeric (meth)acryl compounds such as, for example, urethane acrylates, polyester acrylates, epoxy acrylates; polyacrylamide analogues of the foregoing; and combinations thereof. Such compounds are widely available from vendors such as, for example, Sartomer Company of Exton, Pa.; UCB Chemicals Corporation of Smyrna, Ga.; Cytec Corporation, Cognis, and Aldrich Chemical Company of Milwaukee, Wis. Additional useful (meth)acrylate materials include hydantoin moiety-containing poly(meth)acrylates, for example, as described in U.S. Pat. No. 4,262,072 (Wendling et al.).

Other compounds that contain at least one ethylenically unsaturated bond include methyl(meth)acrylate, ethyl(meth) acrylate, isopropyl(meth)acrylate, n-hexyl(meth)acrylate, stearyl(meth)acrylate, allyl(meth)acrylate, 1,3-propanediol di(meth)acrylate, trimethylolpropane tri(meth)acrylate, 1,2, 4-butanetriol tri(meth)acrylate, 1,4-cyclohexanediol di(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, and trishydroxyethylisocyanurate tri(meth)acrylate; (meth)acrylamides (i.e., acrylamides and methacrylamides) such as (meth)acrylamide, methylene bis-(meth)acrylamide, and diacetone(meth) acrylamide; urethane(meth)acrylates; and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free-radically polymerizable compounds can be used if desired.

The curable (e.g. dental) composition may also contain hydroxyl groups and ethylenically unsaturated groups in a single molecule. Examples of such materials include hydroxyalkyl(meth)acrylates, such as 2-hydroxyethyl(meth) acrylate and 2-hydroxypropyl(meth)acrylate; glycerol mono- or di-(meth)acrylate; trimethylolpropane mono- or di-(meth) acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are also available from a wide variety of commercial sources, such as Sigma-Aldrich, St. Louis.

In certain embodiments curable components can include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate).

An initiator is typically added to the multifunctional polymerizable ionic liquid or to the mixture of polymerizable ingredients comprising at least one multifunctional polymerizable ionic liquid, as described herein. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

In some embodiments, the multifunctional polymerizable ionic liquid or composition comprising such is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroboarate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate. Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N,N-dimethylaminoethyl methacrylate. When present, the amine reducing agent is present in the photopolymerizable composition in an amount from about 0.1 weight percent to about 5.0 weight percent, based on the total weight of the composition.

In some preferred embodiments, the curable composition may be irradiated with ultraviolet (UV) rays. For this embodiment, suitable photoinitiators are those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis (2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably an ultraviolet or visible light source. It is convenient to employ light sources that emit actinic radiation light between 20 nm and 800 nm such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The multifunctional polymerizable ionic liquid or compositions comprising such may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems, thermally curing systems and combinations thereof. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

The compositions can also be cured with a thermally or heat activated free radical initiator. Typical thermal initiators include peroxides such as benzoyl peroxide and azo compounds such as azobisisobutyronitrile.

In some embodiments, such as when the composition comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

In such compositions comprising appreciable amounts of filler, the one or more multifunctional polymerizable ionic liquids are typically present in an amount totaling at least 5 wt-%, 6 wt-%, 7 wt-%, 8 wt-%, 9 wt-%, or 10 wt-%, based on the total weight of the composition. The concentration of multifunctional polymerizable ionic liquids is generally no greater than about 60 wt-%. In some embodiments the total amount of multifunctional polymerizable ionic liquids is at most 40 wt-%, preferably at most 30 wt-%, and more preferably at most 25 wt-%.

Fillers may be selected from one or more of a wide variety of materials, as known in the art, and include organic and inorganic filler.

The filler can be an inorganic material. It can also be a crosslinked organic material that is insoluble in the polymerizable resin, and is optionally filled with inorganic filler. The filler can be radiopaque, radiolucent, or nonradiopaque. Fillers can be ceramic in nature.

Inorganic filler particles include quartz (i.e., silica), submicron silica, zirconia, submicron zirconia, and non-vitreous microparticles of the type described in U.S. Pat. No. 4,503,169 (Randklev).

Filler components include nanosized silica particles, nanosized metal oxide particles, and combinations thereof. Nanofillers are also described in U.S. Pat. Nos. 7,090,721 (Craig et al.), 7,090,722 (Budd et al.), 7,156,911 (Kangas et al.), and 7,649,029 (Kolb et al.).

Examples of suitable organic filler particles include filled or unfilled pulverized polycarbonates, polyepoxides, poly(meth)acrylates and the like. Commonly employed filler particles are quartz, submicron silica, and non-vitreous microparticles of the type described in U.S. Pat. No. 4,503,169 (Randklev).

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

In some embodiments, the composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some embodiments, the nanoparticles are in the form of nanoclusters, i.e. a group of two or more particles associated by relatively weak intermolecular forces that cause the particles to clump together, even when dispersed in the resin. Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_m Si(OR)_n$ or $CH_2=C(CH_3)_m C=OOASi(OR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT,), and other similar ingredients that will be apparent to those skilled in the art. The curable composition may comprises various other ethylenically unsaturated monomer(s), oligomer(s), and polymer(s) and additive as known in the art, such as described in U.S. Provisional Application Ser. No. 61/289,098 titled "CURABLE DENTAL COMPOSITIONS AND ARTICLES COMPRISING POLYMERIZABLE IONIC LIQUIDS"; incorporated herein by reference.

The present invention will be further illustrated with reference to a dental composition as an illustrative composition having high mechanical strength. Articles, such as dental composites, can be made from a curable composition by casting (e.g. a highly filled) curable composition in contact with a mold and curing the composition. Articles, such as dental composites, can alternatively be made by first curing the composition and then mechanically milling the composition into the desired article.

The curable blends of polymerizable ionic liquid in combination with convention (e.g. (meth)acrylate) ethylenically unsaturated monomers can be used for a variety of other uses, particularly (e.g. photo) curable coatings. A coated article can be prepared by applying the composition described herein to a substrate and curing the composition.

The curable blends can be applied to a variety of substrates. Suitable substrate materials include inorganic substrates such as glass or ceramics, natural and synthetic organic substrates such as paper, wood, as well as thermosetting or thermoplastic polymers such as polycarbonate, poly(meth)acrylate (e.g., polymethyl methacrylate or "PMMA"), polyolefins (e.g., polypropylene or "PP"), polyurethane, polyesters (e.g., polyethylene terephthalate or "PET"), polyamides, polyimides, phenolic resins, cellulose diacetate, cellulose triacetate, polystyrene, styrene-acrylonitrile copolymers, epoxies, and the like. The substrate thickness typically also will depend on the intended use. For most applications, substrate thicknesses of less than about 0.5 mm are preferred, and more preferably about 0.02 to about 0.2 mm. The substrate can be treated to improve adhesion between the substrate and curable coating compositions, e.g., chemical treatment, corona treatment such as air or nitrogen corona, plasma, flame, or actinic radiation. If desired, an optional tie layer or (e.g. polymerizable ionic liquid based) primer can be applied to the substrate to increase the interlayer adhesion.

The curable coating composition can be applied using a variety of conventional coating methods. Suitable coating methods include, for example, spin coating, knife coating, die coating, wire coating, flood coating, padding, spraying, roll coating, dipping, brushing, foam application, and the like.

The coating is dried, typically using a forced air oven. The dried coating is at least partially and typically completely cured using an energy source.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

Example 1

A mixture of 2-methacryloxyethyl acrylate (prepared according to Klee, J. E., Neidhart, F., Flammersheim, H. J., and Mulhaupt, R., *Macromol. Chem. Phys.* 200, 517-523 (1999), 15.00 g, 81 mmol) and imidazole (5.54 g, 81 mmol) were heated to 85° C. for one hour to give a (imidazole Michael adduct intermediate) yellow liquid.

4.94 g (20 mmol) of the imidazole Michael adduct intermediate compound, just described, was mixed with 4.6 g (20 mmol) of mono-2-(methacryloxy)ethyl phthalate (Aldrich) in a flask for 3 hours, viscous ionic liquid obtained.

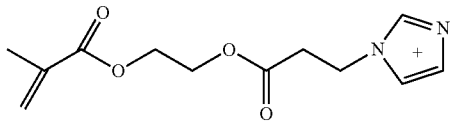

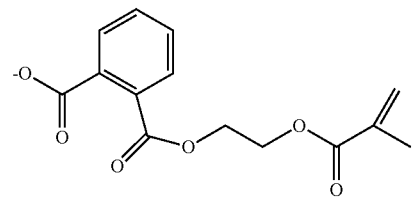

Example 2

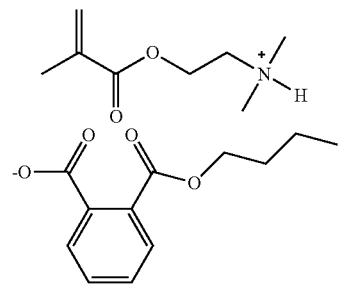

A mixture of dimethylaminoethyl methacrylate (Aldrich, 70.739 g, 0.45 mol), Prostab 5198 (Ciba, 17 mg), and monobutyl phthalate (Eastman, 100.00 g, 0.45 mol) was placed in a jar. The jar was capped and rolled at room temperature for 17 hours. A yellow oil was obtained.

Example 3

A mixture of dimethylaminoethyl acrylate (Aldrich, 64.43 g, 0.45 mol), Prostab 5198 (17 mg), and mono-butyl phthalate (Eastman, 100.00 g, 0.45 mol) was placed in a jar. The jar was capped and rolled at room temperature for 17 hours. A brown oil was obtained.

Example 4

A mixture of dimethylaminoethyl methacrylate (56.62 g, 0.36 mol), Prostab 5198 (17 mg), and mono-2-(methacryloxy)ethyl phthalate (Aldrich, 100.00 g, 0.36 mol) was placed in a jar. The jar was capped and rolled at room temperature for 17 hours. A colorless oil was obtained.

Example 5

A mixture of dimethylaminoethyl acrylate (51.47 g, 0.36 mol), Prostab 5198 (17 mg), and mono-2-(methacryloxy) ethyl phthalate (100.00 g, 0.36 mol) was placed in a jar. The jar was capped and rolled at room temperature for 17 hours. A colorless oil was obtained.

Example 6

A mixture of diethylaminoethyl methacrylate (TCI, 33.41 g, 0.18 mol), Prostab 5198 (8 mg), and mono-2-(methacryloxy)ethyl phthalate (50.00 g, 0.18 mol) was placed in a jar. The jar was capped and rolled at room temperature for 3 hours. A colorless oil was obtained.

Example 7

To a mechanically stirred mixture of phthalic anhydride (Aldrich, 50.00 g, 0.34 mol), 4-hydroxybutyl acrylate (San Esters Corporation, 48.67 g, 0.34 mol), Prostab 5198 (7 mg), and methylene chloride (250 mL) was added triethylamine (Alfa Aesar, 34.16 g, 0.34 mol) dropwise over 1 hour. The mixture was then stirred for 17 hours at room temperature. The solvent was removed under vacuum. Additional triethylamine (5.52 g) was added to the mixture to replace some of

Example 8

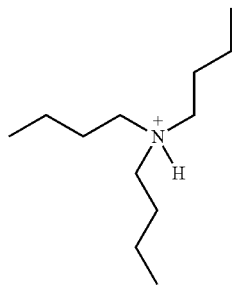

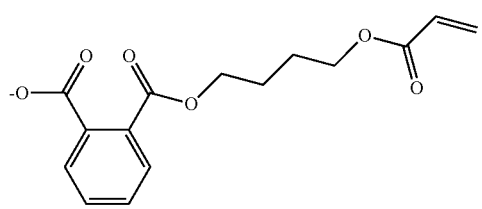

To a mechanically stirred mixture of phthalic anhydride (50.00 g, 0.34 mol), 4-hydroxybutyl acrylate (48.67 g, 0.34 mol), Prostab 5198 (7 mg), and methylene chloride (250 mL) was added tributylamine (Alfa Aesar, 62.65 g, 0.34 mol) dropwise over 1 hour. The mixture was then stirred for 17 hours at room temperature. The solvent was removed under vacuum. A yellow oil was obtained.

Example 9

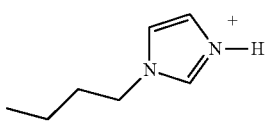

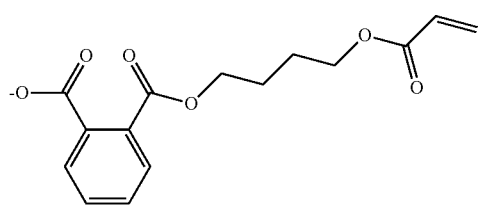

To a mechanically stirred mixture of phthalic anhydride (50.00 g, 0.34 mol), 4-hydroxybutyl acrylate (48.67 g, 0.34 mol), Prostab 5198 (7 mg), and methylene chloride (250 mL) was added butyl imidazole (Lancaster, 41.97 g, 0.34 mol) dropwise over 1 hour. The mixture was then stirred for 17 hours at room temperature. The solvent was removed under vacuum. A yellow oil was obtained.

Example 10

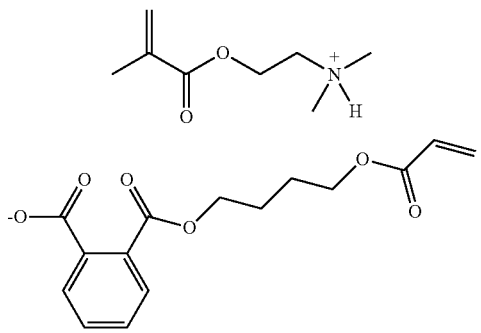

To a mechanically stirred mixture of phthalic anhydride (50.00 g, 0.34 mol), 4-hydroxybutyl acrylate (48.67 g, 0.34 mol), Prostab 5198 (7 mg), and methylene chloride (250 mL) was added dimethyl aminoethylmethacrylate (48.39 g, 0.34 mol) dropwise over 1 hour. The mixture was then stirred for 17 hours at room temperature. The solvent was removed under vacuum. A yellow oil was obtained.

Example 11

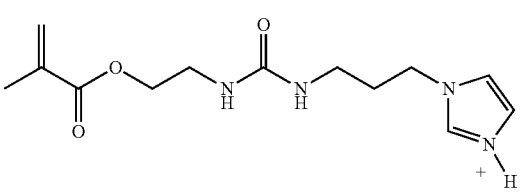

A mixture of N,N-dimethyl vinyl benzylamine (mixture of isomers, Aldrich, 1.000 g, 6.2 mmol) and mono-2-(methacryloxy)ethyl phthalate (1.726 g (6.2 mmol) was placed in a vial. After mixing for 5 minutes a liquid product was obtained.

Example 12

27

-continued

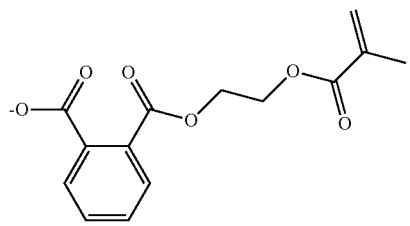

N-(3-aminopropyl)imidazole (Alfa Aesar, 2.55 g, 0.02 mol) and tetrahydrofuran (Alfa Aesar, 30 mL) were placed an a flask with magnetic stirring. 2-Isocyanatoethyl methacrylate (Showa Denko, Japan, 3.26 g, 0.02 mol) was added dropwise over 30 minutes while cooling the flask in an ice water bath. After three hours, mono-2-(methacryloxy)ethyl phthalate (5.67 g, 0.02 mol) and tetrahydrofuran (10 mL) were added and the mixture was stirred for three hours at room temperature. The solvent was removed under vacuum to give thick liquid product.

Example 13

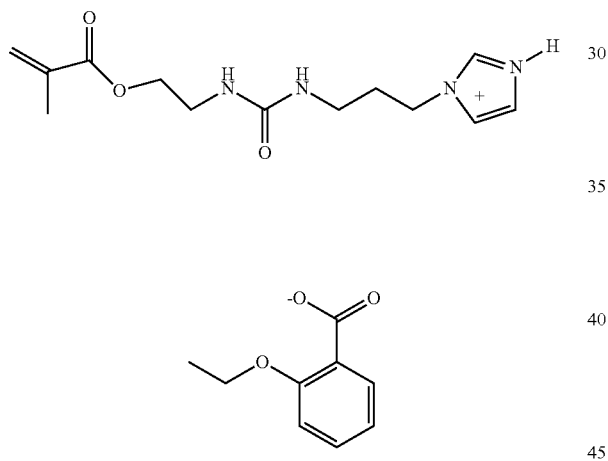

N-(3-aminopropyl)imidazole (Alfa Aesar, 2.55 g, 0.02 mol) and tetrahydrofuran (Alfa Aesar, 30 mL) were placed an a flask with magnetic stirring. 2-Methacryloyloxyethyl isocyanate (Showa Denko, Japan, 3.26 g, 0.02 mol) was added dropwise over 30 minutes while cooling the flask in an ice water bath. After three hours, 2-ethoxybenzoic acid (3.39 g, 0.02 mol) and tetrahydrofuran (10 mL) were added and the mixture was stirred for another three hours at room temperature. The solvent was removed under vacuum to give viscous liquid product.

Example 14

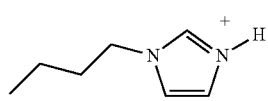

28

-continued

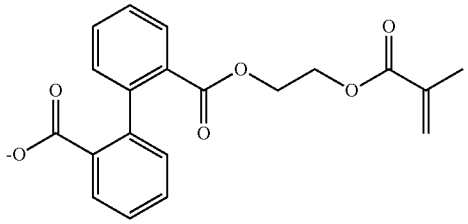

Diphenic anhydride (Aldrich, 11.21 g, 0.05 mol), 2-hydroxyethyl methacrylate (6.70 g, 0.05 mol), BHT (60 mg), and toluene (20 mL) were mixed at room temperature. The suspension was heated at 90° C. for 5.5 hours. The solid dissolved after 3.5 hours. The mixture was cooled to room temperature and the solvent was removed under vacuum. A colorless viscous liquid was obtained as product (Yield of 17.7 g).

The product from the reaction above (3.54 g) and 1-butyl imidazole (1.24 g, 0.01 mol) were mixed together. A viscous colorless liquid was obtained as the product.

Example 15

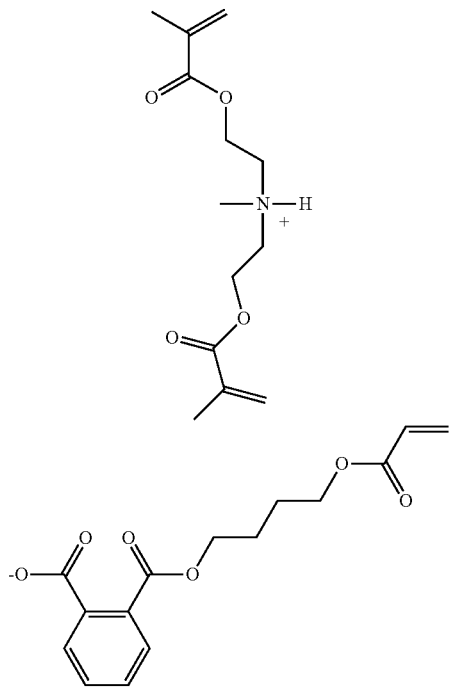

Methacrylic anhydride (TCI, 155.65 g, 1.0 mol) was added dropwise over 1.5 hours to N-methyl diethanolamine (Aldrich, 50.03 g, 0.42 mol). The temperature increased to 70° C. during the addition. The mixture was then stirred at room temperature for 17 hours. Ethyl acetate (600 mL) was added and the mixture was washed with a solution of sodium hydroxide (50 g) in water (300 mL). The organic phase was separated and concentrated under vacuum to give an oil. Phenothiazine (0.25 g) was added and the crude oil was distilled under reduced pressure. The product (N-methyl dimethacryloxyethyl amine) was collected as a colorless oil (90-91° C. @0.05 mmHg, yield of 76.91 g).

A mixture of mono-2-(methacryloxy)ethyl phthalate (2.18 g, 7.8 mmol), N-methyl dimethacryloxyethyl amine (2.00 g, 7.8 mmol), and Prostab 5198 (2 mg) was placed in a vial. The vial was capped and mixed at room temperature for 10 minutes. A yellow oil was obtained.

Determination of Air to Nitrogen Curing Exotherm Ratio (Visible Light Polymerization:

The photo polymerization behavior of monomers under N2 and air was examined using differential scanning photocalorimetry (photo DSC). The photo DSC was a TA instrument (New Castle, Del.) with DSC module 2920. The light source was a mercury/argon lamp with an Oriel PN 59480 425 nm long pass light filter. The light intensity was 3 mW/cm$^2$, measured using an International Light light meter Model IL 1400 equipped with a Model XRL, 340A detector. The photo curable samples contained 0.5% camphorquinone (Sigma-Aldrich), 1.0% ethyl 4-(N,N-dimethylamino)benzoate (Sigma-Aldrich) and 1.0% diphenyl iodium hexafluorophosphate as the photoinitiator package. A 10 mg cured sample was used as a reference.

About 10 mg of the sample was weighed accurately for the testing with a Hermetic Pan (aluminum sample pan) as the sample holder. The samples were equilibrated at 37° C. for 5 minutes, and then the light aperture was opened to irradiate the sample. During irradiation the sample temperature was held at 37° C. The total irradiation time was 30 minutes. After 30 minutes, the aperture was closed and the sample maintained at 37° C. for another 5 minutes. The samples were tested under nitrogen and air atmosphere respectively.

The data was collected as heat output per unit weight (mW/g). The data was analyzed using TA Thermal Solutions Universal Analysis software.

Monomers were run once under nitrogen, then an identical sample was run under air. The DSC recorded the heat generation from the curing sample during exposure, and the area under the curve was integrated to give total Joules/gram of the monomer. The heat generated when the sample was cured in air was divided by the heat generated when the sample was cured in nitrogen to give the curing ratio. A higher ratio represents less oxygen inhibition.

Determination of Air to Nitrogen Curing Exotherm Ratio (UV Polymerization)

Each monomer was mixed with 0.1 wt % photoinitiator 1-819 (BASF, Germany). Approximately 15 mg of each of sample was placed in open hermetic aluminum DSC pans (TA instruments TO91209). Pans were then placed on one of the posts of a differential photocalorimeter (DPC 2920, TA Instruments) while an empty DSC pan was placed on the reference post. A mask was placed over the DSC posts so that radiation coming from the overhead UV lamp would only directly contact the individual DSC pans. A Quartz glass panel was then placed over the mask to enclose the chamber which was then purged with either nitrogen or oxygen at a rate of 1000 cm$^3$/min. The chamber door was closed and allowed to purge for 10 minutes. The UV lamp (14 mW/cm$^2$) was then switched on for exactly 10 minutes.

The heat flow profile of each sample photopolymerization was integrated, after first subtracting the heat generated by the UV lamp baseline, to yield the total heat released from each sample. The total heat released was then normalized by dividing by the weight of the monomer initially placed in the DSC pan. The ratio of polymerization heat released per unit gram for the each monomer sample in air vs. nitrogen was then calculated.

Testing Results for Photocuring a Multifunctional PIL Comprising a Polymerizable Cation and Polymerizable Anion by Photo DSC

|  | Curing ratio (air/N2) Visible Light Polymerization | Curing ratio (air/N2) UV Polymerization |
|---|---|---|
| 100 wt % Example 4 | 0.97 | |
| 100 wt % Example 5 | 1.00 | |
| 100 wt % Example 11 | 0.94 | |
| 100 wt % Example 12 | 0.98 | |
| 100 wt % Example 2 | | 0.98 |
| 100 wt % Example 4 | | 0.97 |

The curing ratio for Example 4 was 0.97 for both visible light and UV polymerization. Example 2 would also exhibit substantially the same curing ratio using the standard visible light polymerization method.

Hardenable Dental Composition

| Abbreviation | Chemical Description (Supplier, Location) |
|---|---|
| | Polymerizable Monomer |
| HEMA | 2-Hydroxyethyl methacrylate (Sigma-Aldrich, St. Louis, MO) |
| VBCP | Polymer made by reacting AA:ITA copolymer with sufficient IEM to convert 16 mole percent of the acid groups of the copolymer to pendent methacrylate groups according to the dry polymer preparation of Example 11 of U.S. Pat. No. 5,130,347. |
| | Components of Photoinitiator Package |
| BHT | 2,6-di-tert-butyl-4-methylphenol (Sigma-Aldrich Fine Chemicals, St. Louis, MO) |
| CPQ | camphorquinone (Sigma-Aldrich) |
| DPIHFP | "DPIHFP" refers to diphenyl iodonium hexafluorophosphate; |

Example 15

Resin Modified Glass Ionomer Restorative

| Part A - Resin Component | grams | Wt-% Resin Component A | Wt-% of Total Composition |
|---|---|---|---|
| PIL Example 4 | 3.99 | 19.95 | 3.99 |
| DI Water | 6.02 | 30.1 | 6.02 |
| CPQ | 0.042 | 0.21 | 0.042 |
| VBCP | 9.73 | 48.65 | 9.73 |
| DPIHFP | 0.196 | 0.98 | 0.196 |
| BHT | 0.0098 | 0.049 | 0.0098 |

Example 16

Resin Modified Glass Ionomer Restorative

| Part A - Resin Component | grams | Wt-% Resin Component A | Wt-% of Total Composition |
|---|---|---|---|
| PIL Example 11 | 3.99 | 19.95 | 3.99 |
| DI Water | 6.02 | 30.1 | 6.02 |

-continued

| Part A - Resin Component | grams | Wt-% Resin Component A | Wt-% of Total Composition |
|---|---|---|---|
| CPQ | 0.042 | 0.21 | 0.042 |
| VBCP | 9.73 | 48.65 | 9.73 |
| DPIHFP | 0.196 | 0.98 | 0.196 |
| BHT | 0.0098 | 0.049 | 0.0098 |

The organic resin component (Part A) of Examples 15 and 16 were each separately mixed in a medium cup for five 2 minute cycles at 3000 rpm. This polymerizable liquid resin mixture was then hand mixed with a FAS glass powder (as described in U.S. Pat. No. 5,154,762) of "Vitremer™ Core Build-Up Materials Restorative" commercially available from 3M™ ESPE™ at a weight ratio 1 to 4 (powder).

A control was made in the same manner except that HEMA was used in place of PIL Example 4.

Diametral Tensile Strength (DTS) Test Method

DTS of a test sample was prepared according to the following procedure. An uncured sample was injected into a 4-mm (inside diameter) glass tube that was capped with silicone rubber plugs; and then the tube was compressed axially at approximately 2.88 kg/cm² pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). Cured samples were allowed to stand for 1 hour at about 37° C./90%+Relative Humidity and then were cut with a diamond saw to form 8-mm long cylindrical plugs for measurement of compressive strength. The plugs were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Five cylinders of cured samples were prepared and measured with the results reported in MPa as the average of the five measurements.

The Dental Composite was compared to a control dental composite composition in which HEMA was used in place of PIL Example 4. The Diametral Tensile Strength was tested as follows:

|  | DTS (Mpa) | Std. Dev. |
|---|---|---|
| Example 15 | 47.5 | 7.2 |
| Example 16 | 48.1 | 2.83 |
| Control Restorative | 42.6 | 6.1 |

Example 17

Wood Coating

A polymerizable ionic liquid coating was prepared by forming a mixture of 3 parts by weight of the polymerizable ionic liquid of Example 4, one part Nanocryl C150 (50% silica nanoparticles in trimethylolpropane triacrylate, available from Nanoresins), one part trimethylolpropane triacrylate (TMPTA) from Sartomer. Photoinitiator was ethyl (2,4,6-trimethylbenzoyl)phenylphosphinate (TPO-L, available from BASF) at a 0.5 weight percent level.

A control wood coating was prepare by forming a mixture of one part Nanocryl C150 and 4 parts of TMPTA (from Sartomer). The photoinitiator was ethyl (2,4,6-trimethylbenzoyl)phenylphosphinate (TPO-L, available from BASF) at a 0.5 weight percent level.

Wooden substrates utilized in these experiments were oak faced plywood platens, sanded sequentially with 100 grit and 220 grit sandpaper.

The coating formulations were applied on the wood substrates with a #12 Meyer rod, then processed on a Fusion Systems UV processor (D bulb, dichroic reflectors) at various line speeds and under an air atmosphere. UV exposure energy was measured as UVA with 2637 mJ/cm², UVB with 674 mJ/cm², UVC with 55 mJ/cm², and UVV 2160 mJ/cm² at line speed at 15 feet/minute.

Cotton tipped applicators were used to scratch the coating surface to determine the extent of curing of the coating.

| Formulation | line speed, feet/minute | cure result |
|---|---|---|
| control | 20 | no |
| Example 17 | 20 | partial |
| control | 10 | fair |
| Example 17 | 10 | good |

The results show that coating comprising the polymerizable ionic liquid exhibited improved curing in air relative to the control.

What is claimed is:

1. A polymerizable ionic liquid comprising a cation and an aromatic carboxylate anion; wherein the cation, anion, or both comprise a free-radically polymerizable group and at least one free-radically polymerizable group is selected from the group consisting of (meth)acrylamide, (meth)acrylate, and vinyl ether.

2. The polymerizable ionic liquid of claim 1 wherein the cation comprises a free-radically polymerizable group selected from the group consisting of (meth)acrylamide, (meth)acrylate, and vinyl ether and the anion lacks a free-radically polymerizable group.

3. The polymerizable ionic liquid of claim 1 wherein the anion comprises a free-radically polymerizable group selected from the group consisting of (meth)acrylamide, (meth)acrylate, and vinyl ether and the cation lacks a free-radically polymerizable group.

4. The polymerizable ionic liquid of claim 1 wherein the anion and cation each comprise at least one free-radically polymerizable group selected from the group consisting of (meth)acrylamide, (meth)acrylate, and vinyl ether.

5. The polymerizable ionic liquid of claim 2 wherein the free-radically polymerizable group is a (meth)acrylate group.

6. The polymerizable ionic liquid of claim 1 wherein the cation is a substituted ammonium or phosphonium cation.

7. The polymerizable ionic liquid of claim 6 wherein the ionic liquid has the general formula:

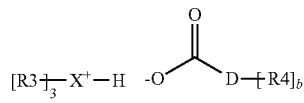

wherein

X is nitrogen or phosphorus;

R3 and R4 are independently alkyl or heteroalkyl, and at least one R3 or R4 comprises a free-radically polymerizable group selected from the group consisting of (meth)acrylamide, (meth)acrylate, and vinyl ether;

D comprises an aromatic moiety and optionally comprises a linking group between the carboxylate end group and aromatic moiety and/or optionally comprises a linking group between the aromatic moiety and R4; and b is 0-2.

8. The polymerizable ionic liquid of claim 7 wherein the free-radically polymerizable groups are (meth)acrylate groups.

9. The polymerizable ionic liquid of claim 7 wherein R3 are alkyl or heteroalkyl groups and R4 comprises the free-radically polymerizable group selected from the group consisting of (meth)acrylamide, (meth)acrylate, and vinyl ether.

10. The polymerizable ionic liquid of claim 7 wherein R4 are alkyl or heteroalkyl groups and at least one R3 comprises a free-radically polymerizable group selected from the group consisting of (meth)acrylamide, (meth)acrylate, and vinyl ether.

11. The polymerizable ionic liquid of claim 7 wherein R3 and R4 both comprise at least one free-radically polymerizable group selected from the group consisting of (meth)acrylamide, (meth)acrylate, and vinyl ether.

12. The polymerizable ionic liquid claim 10 wherein R3 comprises at least two polymerizable groups selected from the group consisting of (meth)acrylamide, (meth)acrylate, and vinyl ether.

13. The ionic liquid of claim 1 wherein the cation is a substituted imidazolium cation.

14. The ionic liquid of claim 13 wherein the ionic liquid has the general formula:

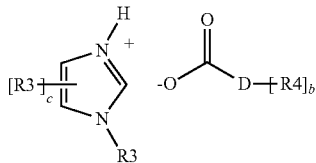

wherein

R3 and R4 are independently alkyl or heteroalkyl, and at least one R3 or R4 comprises a free-radically polymerizable group selected from the group consisting of (meth)acrylamide, (meth)acrylate, and vinyl ether;

D comprises an aromatic moiety and optionally comprises a linking group between the carboxylate end group and aromatic moiety and/or optionally comprises a linking group between the aromatic moiety and R4;

c is 0 to 3; and b is 0-2.

15. The polymerizable ionic liquid of claim 14 wherein the free-radically polymerizable groups are (meth)acrylate groups.

16. The polymerizable ionic liquid of claim 14 wherein R3 are alkyl or heteroalkyl groups and R4 comprises a free-radically polymerizable group selected from the group consisting of (meth)acrylamide, (meth)acrylate, and vinyl ether.

17. The polymerizable ionic liquid of claim 14 wherein R4 are alkyl or heteroalkyl groups and R3 comprises a free-radically polymerizable group selected from the group consisting of (meth)acrylamide, (meth)acrylate, and vinyl ether.

18. The polymerizable ionic liquid of claim 14 wherein R3 and R4 both comprise a free-radically polymerizable group selected from the group consisting of (meth)acrylamide, (meth)acrylate, and vinyl ether.

19. The polymerizable ionic liquid of claim 7 wherein D comprises one, two, or three aromatic rings that are optionally fused.

20. The ionic liquid of claim 1 wherein the ionic liquid has an air to nitrogen curing exotherm of at least 0.90.

21. The ionic liquid of claim 1 wherein the polymerizable ionic liquid has a melting point below 25° C.

22. A curable composition wherein the composition comprises at least one polymerizable ionic liquid according to claim 1 and at least one other free-radically polymerizable monomer, oligomer, or polymer.

23. The polymerizable ionic liquid of claim 7 wherein two R3 groups are alkyl, one R3 comprises a free-radically polymerizable group, and R4 comprises a free-radically polymerizable group selected from the group consisting of (meth)acrylamide, (meth)acrylate, and vinyl ether.

24. The polymerizable ionic liquid of claim 23 wherein the R3 comprising the free-radically polymerizable group further comprises an aromatic linking group.

* * * * *

UNITED STATES PATENT AND TRADEMARK OFFICE
CERTIFICATE OF CORRECTION

PATENT NO. : 8,552,130 B2  
APPLICATION NO. : 13/579153  
DATED : October 8, 2013  
INVENTOR(S) : Kevin M. Lewandowski et al.

Page 1 of 2

It is certified that error appears in the above-identified patent and that said Letters Patent is hereby corrected as shown below:

On the Title Page, Column 2, Item (56)
Line 4, Delete "Hexy1" and insert -- Hexyl --, therefor.

Title Page 2, Column 1, Item (56)
Line 47, Delete "Polyer" and insert -- Polymer --, therefor.

Title Page 2, Column 2, Item (56)
Line 15, Delete "Termally" and insert -- Thermally --, therefor.

In the Specification

Column 1
Line 60, Delete "crosslinking" and insert -- crosslinking. --, therefor.

Column 2
Line 2, Delete "thereof" and insert -- thereof; --, therefor.
Line 4, Delete "thereof" and insert -- thereof; --, therefor.

Column 4
Line 36, Delete "an a" and insert -- a --, therefor.

Column 5
Line 1-10, Delete ", and" and insert -- . --, therefor.

Column 9
Line 63, Delete "methylpyrrole," and insert -- methyl pyrrole, --, therefor.

Column 11
Line 48, Delete "ethy" and insert -- ethyl --, therefor.

Signed and Sealed this
Eighth Day of April, 2014

Michelle K. Lee
*Deputy Director of the United States Patent and Trademark Office*

Line 51, Delete "methylheptyamine," and insert -- methylheptylamine, --, therefor Column 12
Line 60, Delete "homophthlic" and insert -- homophthalic --, therefor.
Line 65, Delete "hydroxylpropyl" and insert -- hydroxypropyl --, therefor.

Column 15
Line 64-65, Delete "pentaerthyritol" and insert -- pentaerythritol --, therefor.

Column 17
Line 21, Delete "tetrafluoroboarate." and insert -- tetrafluoroborate. --, therefor.

Column 27
Line 13, Delete "an" and insert -- on --, therefor.
Line 48, Delete "an" and insert -- on --, therefor.

Column 29
Line 46, Delete "1-819" and insert -- I-819 --, therefor.

Column 30
Line 33, Delete "Photointiator" and insert -- Photoinitiator --, therefor.

In the Claims

Column 33
Line 24, In Claim 12, Delete "liquid" and insert -- liquid of --, therefor.